(12) United States Patent
Bissell et al.

(10) Patent No.: US 7,666,850 B2
(45) Date of Patent: Feb. 23, 2010

(54) DRUG SCREENS BASED ON THE NEWLY FOUND ROLE OF DYSTROGLYCAN PROTEOLYSIS AND RESTORATION OF DYSTROGLYCAN FUNCTION THEREOF

(75) Inventors: Mina J. Bissell, Berkeley, CA (US); John L. Muschler, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 251 days.

(21) Appl. No.: 11/150,406

(22) Filed: Jun. 9, 2005

(65) Prior Publication Data

US 2005/0250164 A1 Nov. 10, 2005

Related U.S. Application Data

(62) Division of application No. 09/652,493, filed on Aug. 31, 2000, now Pat. No. 6,982,151.

(60) Provisional application No. 60/151,766, filed on Aug. 31, 1999.

(51) Int. Cl.
*A61K 48/00* (2006.01)
*G01N 33/536* (2006.01)

(52) U.S. Cl. .................. 514/44; 435/7.23
(58) Field of Classification Search .......... None
See application file for complete search history.

(56) References Cited

U.S. PATENT DOCUMENTS 5,449,616 A 9/1995 Campbell et al.

OTHER PUBLICATIONS

Dermer, GB., "Another Anniversary for the War on Cancer," *Bio/Technology*, vol. 12, pp. 320, (Mar. 12, 1994).

Durbeej, et al., "Non-Muscle α-Dystroglycan Is Involved in Epithelial Development," *Jnl. of Cell Biology*., The Rockefeller University Press (USA), vol. 130, No. 1, pp. 79-91, (Jul. 2, 1995).

Henry, et al., A Role for Dystroglycan in Basement Membrane Assembly, *Cell*, vol. 95, pp. 859-870, (Dec. 11, 1998).

Henry, et al., "Reduced Expression of Dystroglycan in Breast and Prostate Cancer," *Human Pathology*, vol. 32, pp. 791-795, (Aug. 2001).

Holt, et al., "Functional Rescue of the Sarcoglycan Complex in the BIO 14.6 Hamster Using s-Sarcoglycan Gene," *Molecular Cell*, vol. 1, pp. 841-848, (May 2, 1998).

Freshney, "Culture of Animal Cells: A Manual of Basic Technique," Alan R. Liss, Inc., New York, p. 4, (1983).

Tockman, et al., "Considerations in Bringing a Cancer Biomarker to Clinical Application," *Cancer Res.*, vol. 52, pp. 2711s-2718s, (May 1, 1992).

Wirth, et al., "Value of prostate-specific antigen as a tumor marker," *Eur Urol.*, vol. 24, Suppl 2:6-12, Abstract Only (1993).

*Primary Examiner*—Misook Yu
(74) *Attorney, Agent, or Firm*—Michelle Chew Wong; Lawrence Berkeley National Laboratory (57) ABSTRACT

The present invention provides methods and compositions for the diagnosis and treatment of cells lacking normal growth arresting characteristic. The present invention demonstrates that many tumor cells lack normal cell surface α-dystroglycan and thereby lack dystroglycan function. Dystroglycan can be lost from the cell surface by proteolytic shedding of a fragment of α-dystroglycan into the surrounding medium. Upon restoration of dystroglycan function and over-expression of the dystroglycan gene, the once tumorigenic cells revert to non-tumorigenic cells which polarize and arrest cell growth in the presence of basement membrane proteins, demonstrating that dystroglycan functions as a tumor marker and suppressor.

5 Claims, 3 Drawing Sheets

Fig. 2

SEQUENCE LISTING

<160> NUMBER OF SEQ ID NOS: 2

<210> SEQ ID NO 1
<211> LENGTH: 5510
<212> TYPE: DNA
<213> ORGANISM: homo sapiens
<220> FEATURE:
<221> NAME/KEY: CDS
<222> LOCATION: (395)..(3079)

<400> SEQUENCE: 1

```
gggccagtcg gcgccgcgcg gagctggccg ctggattggc tgcaacactc gcgtgtcagg      60
cggttgctag gctccggccg cgcgccccgc ccttgcgctc agcgccctct caccgcccgg     120
tacgtgctcg cgcgaaggct gcggcgcggc gctcgcgcct cttaggcttg gcggtggcgg     180
cggcggcagc ttcgcgccga atccccgggg agcggcggtg gcggcgtcct ggggccagga     240
ggagcgaaca cctgccgcgg tcctcccgcc ggcgctgggc tctgtgtgct ccgggatgga     300
gcaggtgtgc agagggtgag aacccagctc tgggaccaag tcacttgctt ccttacttag     360
caagactatc gacttgagca aacttggacc tggg atg agg atg tct gtg ggc ctc     415
                                    Met Arg Met Ser Val Gly Leu
                                      1               5 tcg ctg ctg ctg ccc ctc tgg ggg agg acc ttt ctc ctc ctg ctc tct       463
Ser Leu Leu Leu Pro Leu Trp Gly Arg Thr Phe Leu Leu Leu Leu Ser
         10                  15                  20 gtg gtt atg gct cag tcc cac tgg ccc agt gaa ccc tca gag gct gtc       511
Val Val Met Ala Gln Ser His Trp Pro Ser Glu Pro Ser Glu Ala Val
     25                  30                  35 agg gac tgg gaa aac cag ctt gag gca tcc atg cac tca gtg ctc tca       559
Arg Asp Trp Glu Asn Gln Leu Glu Ala Ser Met His Ser Val Leu Ser
 40                  45                  50                  55 gac ctc cac gag gct gtt ccc aca gtg gtt ggc att cct gat ggc acg       607
Asp Leu His Glu Ala Val Pro Thr Val Val Gly Ile Pro Asp Gly Thr
                 60                  65                  70 gct gtc gtc ggg cgc tca ttt cga gtg acc att cca aca gat ttg att       655
Ala Val Val Gly Arg Ser Phe Arg Val Thr Ile Pro Thr Asp Leu Ile
             75                  80                  85 gcc tcc agt gga gat atc atc aag gta tca gcg gca ggg aag gag gct       703
Ala Ser Ser Gly Asp Ile Ile Lys Val Ser Ala Ala Gly Lys Glu Ala
         90                  95                 100 ttg cca tct tgg ctg cac tgg gac tca cag agc cac acc ctg gag ggc       751
Leu Pro Ser Trp Leu His Trp Asp Ser Gln Ser His Thr Leu Glu Gly
    105                 110                 115 ctc ccc ctt gac act gat aag ggt gtg cat tac att tca gtg agc gct       799
Leu Pro Leu Asp Thr Asp Lys Gly Val His Tyr Ile Ser Val Ser Ala
120                 125                 130                 135 aca cgg ctg ggg gcc aac ggg agc cac atc ccc cag acc tcc agt gtg       847
Thr Arg Leu Gly Ala Asn Gly Ser His Ile Pro Gln Thr Ser Ser Val
                140                 145                 150 ttc tcc atc gag gtc tac cct gaa gac cac agt gat ctg cag tcg gtg       895
Phe Ser Ile Glu Val Tyr Pro Glu Asp His Ser Asp Leu Gln Ser Val
            155                 160                 165 agg aca gcc tcc cca gac cct ggt gag gtg gta tca tct gcc tgt gct       943
Arg Thr Ala Ser Pro Asp Pro Gly Glu Val Val Ser Ser Ala Cys Ala
        170                 175                 180 gcg gat gaa cct gtg act gtt ttg acg gtg att ttg gat gcc gac ctc       991
Ala Asp Glu Pro Val Thr Val Leu Thr Val Ile Leu Asp Ala Asp Leu
    185                 190                 195
```

```
acc aag atg acc cca aag caa agg att gac ctc ctg cac agg atg cgg     1039
Thr Lys Met Thr Pro Lys Gln Arg Ile Asp Leu Leu His Arg Met Arg
200             205                 210                 215 agc ttc tca gaa gta gag ctt cac aac atg aaa tta gtg ccg gtg gtg     1087
Ser Phe Ser Glu Val Glu Leu His Asn Met Lys Leu Val Pro Val Val
                220                 225                 230 aat aac aga cta ttt gac atg tcg gcc ttc atg gct ggc ccg gga aat     1135
Asn Asn Arg Leu Phe Asp Met Ser Ala Phe Met Ala Gly Pro Gly Asn
            235                 240                 245 cca aaa aag gtg gtg gag aat ggg gcc ctt ctc tcc tgg aag ctg ggc     1183
Pro Lys Lys Val Val Glu Asn Gly Ala Leu Leu Ser Trp Lys Leu Gly
250                 255                 260 tgc tcc ctg aac cag aac agt gtg cct gac att cat ggt gta gag gcc     1231
Cys Ser Leu Asn Gln Asn Ser Val Pro Asp Ile His Gly Val Glu Ala
265                 270                 275 cct gcc agg gag ggc gca atg tct gct cag ctt ggc tac cct gtg gtg     1279
Pro Ala Arg Glu Gly Ala Met Ser Ala Gln Leu Gly Tyr Pro Val Val
280                 285                 290                 295 ggt tgg cac atc gcc aat aag aag ccc cct ctt ccc aaa cgc gtc cgg     1327
Gly Trp His Ile Ala Asn Lys Lys Pro Pro Leu Pro Lys Arg Val Arg
                300                 305                 310 agg cag atc cat gct aca ccc aca cct gtc act gcc att ggg ccc cca     1375
Arg Gln Ile His Ala Thr Pro Thr Pro Val Thr Ala Ile Gly Pro Pro
            315                 320                 325 acc acg gct atc cag gag ccc cca tcc agg atc gtg cca acc ccc aca     1423
Thr Thr Ala Ile Gln Glu Pro Pro Ser Arg Ile Val Pro Thr Pro Thr
        330                 335                 340 tct cca gcc att gct cct cca aca gag acc atg gct cct cca gtc agg     1471
Ser Pro Ala Ile Ala Pro Pro Thr Glu Thr Met Ala Pro Pro Val Arg
345                 350                 355 gat cct gtt cct ggg aaa ccc acg gtc acc atc cgg act cga ggc gcc     1519
Asp Pro Val Pro Gly Lys Pro Thr Val Thr Ile Arg Thr Arg Gly Ala
360                 365                 370                 375 att att caa acc cca acc cta ggc ccc atc cag cct act cgg gtg tca     1567
Ile Ile Gln Thr Pro Thr Leu Gly Pro Ile Gln Pro Thr Arg Val Ser
            380                 385                 390 gaa gct ggc acc aca gtt cct ggc cag att cgc cca acg atg acc att     1615
Glu Ala Gly Thr Thr Val Pro Gly Gln Ile Arg Pro Thr Met Thr Ile
        395                 400                 405 cct ggc tat gtg gag cct act gca gtt gct acc cct ccc aca acc acc     1663
Pro Gly Tyr Val Glu Pro Thr Ala Val Ala Thr Pro Pro Thr Thr Thr
    410                 415                 420 acc aag aag cca cga gta tcc aca cca aaa cca gca acg cct tca act     1711
Thr Lys Lys Pro Arg Val Ser Thr Pro Lys Pro Ala Thr Pro Ser Thr
425                 430                 435 gac tcc acc acc acc acg act cgc agg cca acc aag aaa cca cgg aca     1759
Asp Ser Thr Thr Thr Thr Thr Arg Arg Pro Thr Lys Lys Pro Arg Thr
440                 445                 450                 455 ccc cgg cca gtg ccc cgg gtc acc acc aaa gtt tcc atc acc aga ttg     1807
Pro Arg Pro Val Pro Arg Val Thr Thr Lys Val Ser Ile Thr Arg Leu
            460                 465                 470 gaa act gcc tca ccg cct act cgt att cgc acc acc acc agt gga gtg     1855
Glu Thr Ala Ser Pro Pro Thr Arg Ile Arg Thr Thr Thr Ser Gly Val
        475                 480                 485 ccc cgt ggc gga gaa ccc aac cag cgc cca gag ctc aag aac cat att     1903
Pro Arg Gly Gly Glu Pro Asn Gln Arg Pro Glu Leu Lys Asn His Ile
    490                 495                 500 gac agg gta gat gcc tgg gtt ggc acc tac ttt gag gtg aag atc ccg     1951
Asp Arg Val Asp Ala Trp Val Gly Thr Tyr Phe Glu Val Lys Ile Pro
505                 510                 515
```

```
tca gac act ttc tat gac cat gag gac acc acc act gac aag ctg aag    1999
Ser Asp Thr Phe Tyr Asp His Glu Asp Thr Thr Thr Asp Lys Leu Lys
520                 525                 530                 535 ctg acc ctg aaa ctg cgg gag cag cag ctg gtg ggc gag aag tcc tgg    2047
Leu Thr Leu Lys Leu Arg Glu Gln Gln Leu Val Gly Glu Lys Ser Trp
                540                 545                 550 gta cag ttc aac agc aac agc cag ctc atg tat ggc ctt ccc gac agc    2095
Val Gln Phe Asn Ser Asn Ser Gln Leu Met Tyr Gly Leu Pro Asp Ser
            555                 560                 565 agc cac gtg ggc aaa cac gag tat ttc atg cat gcc aca gac aag ggg    2143
Ser His Val Gly Lys His Glu Tyr Phe Met His Ala Thr Asp Lys Gly
        570                 575                 580 ggc ctg tcg gct gtg gat gcc ttc gag atc cac gtc cac agg cgc ccc    2191
Gly Leu Ser Ala Val Asp Ala Phe Glu Ile His Val His Arg Arg Pro
585                 590                 595 caa ggg gat agg gct cct gca agg ttc aag gcc aag ttt gtg ggt gac    2239
Gln Gly Asp Arg Ala Pro Ala Arg Phe Lys Ala Lys Phe Val Gly Asp
600                 605                 610                 615 ccg gca ctg gtg ttg aat gac atc cac aag aag att gcc ttg gta aag    2287
Pro Ala Leu Val Leu Asn Asp Ile His Lys Lys Ile Ala Leu Val Lys
                620                 625                 630 aaa ctg gcc ttc gcc ttt gga gac cga aac tgt agc acc atc acc ctg    2335
Lys Leu Ala Phe Ala Phe Gly Asp Arg Asn Cys Ser Thr Ile Thr Leu
            635                 640                 645 cag aat atc acc cgg ggc tcc atc gtg gtg gaa tgg acc aac aac aca    2383
Gln Asn Ile Thr Arg Gly Ser Ile Val Val Glu Trp Thr Asn Asn Thr
        650                 655                 660 ctg ccc ttg gag ccc tgc ccc aag gag cag atc gct ggg ctg agc cgc    2431
Leu Pro Leu Glu Pro Cys Pro Lys Glu Gln Ile Ala Gly Leu Ser Arg
665                 670                 675 cgg atc gct gag gat gat gga aaa cct cgg cct gcc ttc tcc aac gcc    2479
Arg Ile Ala Glu Asp Asp Gly Lys Pro Arg Pro Ala Phe Ser Asn Ala
680                 685                 690                 695 cta gag cct gac ttt aag gcc aca agc atc act gtg acg ggc tct ggc    2527
Leu Glu Pro Asp Phe Lys Ala Thr Ser Ile Thr Val Thr Gly Ser Gly
                700                 705                 710 agt tgt cgg cac cta cag ttt atc cct gtg gta cca ccc agg aga gtg    2575
Ser Cys Arg His Leu Gln Phe Ile Pro Val Val Pro Pro Arg Arg Val
            715                 720                 725 ccc tca gag gcg ccg ccc aca gaa gtg cct gac agg gac cct gag aag    2623
Pro Ser Glu Ala Pro Pro Thr Glu Val Pro Asp Arg Asp Pro Glu Lys
        730                 735                 740 agc agt gag gat gat gtc tac ctg cac aca gtc att ccg gcc gtg gtg    2671
Ser Ser Glu Asp Asp Val Tyr Leu His Thr Val Ile Pro Ala Val Val
745                 750                 755 gtc gca gcc atc ctg ctc att gct ggc atc att gcc atg atc tgc tac    2719
Val Ala Ala Ile Leu Leu Ile Ala Gly Ile Ile Ala Met Ile Cys Tyr
760                 765                 770                 775 cgc aag aag cgg aag ggc aag ctt acc ctt gag gac cag gcc acc ttc    2767
Arg Lys Lys Arg Lys Gly Lys Leu Thr Leu Glu Asp Gln Ala Thr Phe
                780                 785                 790 atc aag aag ggg gtg cct atc atc ttt gca gac gaa ctg gac gac tcc    2815
Ile Lys Lys Gly Val Pro Ile Ile Phe Ala Asp Glu Leu Asp Asp Ser
            795                 800                 805 aag ccc cca ccc tcc tcc agc atg cca ctc att ctg cag gag gag aag    2863
Lys Pro Pro Pro Ser Ser Ser Met Pro Leu Ile Leu Gln Glu Glu Lys
        810                 815                 820 gct ccc cta ccc cct cct gag tac ccc aac cag agt gtg ccc gag acc    2911
Ala Pro Leu Pro Pro Pro Glu Tyr Pro Asn Gln Ser Val Pro Glu Thr
825                 830                 835
```

```
act cct ctg aac cag gac acc atg gga gag tac acg ccc ctg cgg gat         2959
Thr Pro Leu Asn Gln Asp Thr Met Gly Glu Tyr Thr Pro Leu Arg Asp
840                 845                 850                 855 gag gat ccc aat gcg cct ccc tac cag ccc cca ccg ccc ttc aca gta         3007
Glu Asp Pro Asn Ala Pro Pro Tyr Gln Pro Pro Pro Pro Phe Thr Val
                860                 865                 870 ccc atg gag ggc aag ggc tcc cgt ccc aag aac atg acc cca tac cgg         3055
Pro Met Glu Gly Lys Gly Ser Arg Pro Lys Asn Met Thr Pro Tyr Arg
            875                 880                 885 tca cct cct ccc tat gtc cca cct taacccgcaa gcgcctgggt ggaggcaggg        3109
Ser Pro Pro Pro Tyr Val Pro Pro
            890                 895 tagggcaggg ccctggagac gacatggtgt tgtctgtgga gaccggtggc ctgcagacca       3169
ttgcccaccg ggagccgaca cctgacctag cacacactga cacaggggcc tggacaagcc       3229
cgccctctct ggtcctccca aaccccaaag cagctggaga ctttgggg actttttttat       3289
ttttattttt tgcctaacag cttttggttt gttcatagag aactcttcgc ttcatttttg       3349
atggctggct ctgaaagcac catgtggagt ggaggtggag ggaccgagga accatgaatg       3409
aactcgcagg cagtgccggg cggcccctg gctctctgcg ttttgccttt aacactaact       3469
gtactgtttt ttctattcac gtgtgtctag ctgcaggatg taacatggaa aacagtaact       3529
aaagattaaa ttcaaaggac tttcagaagt taaggttaag ttttacgtt taatctgctg       3589
tttacctaaa cttgtatgta aatttttgg gtgggtatgg ggaattgctt tgctaaaaat       3649
aagctcccag ggtgtttcaa acttagaaa gaccaaggga cagtatttt tatcaaagga        3709
atactatttt ttcacactac gtcaacttgg ttgctctgat accccagagc ctgattgggg      3769
gcctcccggc cctggctcac gccaagtccc tggtgctggg tttgctctcc cgctgttgcc      3829
aggggctgga agctggaggg gtctcttggg ccatggacat ccccacttcc agcccatgta      3889
cactagtggc ccacgaccaa ggggtcttca tttccatgaa aaaggactc caagaggcag       3949
tggtggctgt ggcccccaac tttggtgctc cagggtgggc caactgcttg tggggcacc       4009
tgggaggtca aagtctcca ccacatcaac ctatttgtt ttacccttt tctgtgcatt         4069
gtttttttt ttcctcctaa aaggaatatc acggttttt gaaacactca gtgggggaca       4129
ttttggtgaa gatgcaatat ttttatgtca tgtgatgctc tttcctcact tgaccttggc      4189
cgctttgtcc taacagtcca cagtcctgcc ccgacccacc ccatcccttt tctctggcac     4249
tccagtccag cttgggcctg aactactgga aaaggtctgg cggctgggga ggagtgccag     4309
caatagttca taataaaaat ctgttagctc tcaaagctaa ttttttacta aagttttat      4369
acagcctcaa attgttttat taaaaaaaag atttaaaatg gtgatgctta cagcagtttg     4429
tacgagctct taagtgttga ttccatggaa ctgacggctt tgcttgtttt gattcttttc     4489
cccctacttt tcctaatggt ttaaattctg gaattacact gggttctt tgcctttttt       4549
agcagaacat ccgtccgtcc atctgcatct ctgtcccatg actcagggc gcccactctg      4609
cttcgattct cctcctgtgg aagaaaccat ttgagcatg acttttcttg atgtctgaag      4669
cgttattttg ggtactttt agggaggaat gcctttcgca ataatgtatc cattcccctg      4729
attgagggtg ggtgggtgga cccaggctcc ctttgcacac agagcagcta cttctaagcc     4789
atatcgactt ttttgcagag gatttgtgtg tcctccctca ggaggggagg cctggtagga    4849
gggggggaga gttctctgtc ctactgctct caagagggca tttcccttg cgccttctcc     4909
cacagggccc agccctctc ccctgcccaa gtccccaggg ggtactctgg agtgagcagt     4969
ccccctgtgg gggagcctgt aaatgcgggc tcagtggacc actggtgact gggctcatgc   5029
```

-continued

```
ctccaagtca gagtttcccc tggtgcccca gagacaggag cacaagtggg atctgacctg   5089
gtgagattat ttctgatgac ctcatcaaaa aataaacaat tcccaatgtt ccaggtgagg   5149
gctttgaaag gccttccaaa cagctccgtc gcccctagca actccaccat tgggcactgc   5209
catgcagaga cgtggctggc ccagaatggc ctgttgccat agcaactgga ggcgatgggg   5269
cagtgaacag aataacaaca gcaacaatgc ctttgcaggc agcctgctcc cctgagcgct   5329
gggctggtga tggccgttgg actctgtgag atggagagcc aatctcacat tcaagtgttc   5389
accaaccact gatgtgtttt tatttccttc tatatgattt taagatgtgt tttctgcatt   5449
ctgtaaagaa acatatcaaa ctaaataaaa gcagtgtctt tattaaaaaa aaaaaaaaa    5509 a                                                                  5510
```

<210> SEQ ID NO 2
<211> LENGTH: 895
<212> TYPE: PRT
<213> ORGANISM: homo sapiens

<400> SEQUENCE: 2

```
Met Arg Met Ser Val Gly Leu Ser Leu Leu Pro Leu Trp Gly Arg
1               5                   10                  15

Thr Phe Leu Leu Leu Ser Val Val Met Ala Gln Ser His Trp Pro
                20                  25                  30

Ser Glu Pro Ser Glu Ala Val Arg Asp Trp Glu Asn Gln Leu Glu Ala
            35                  40                  45

Ser Met His Ser Val Leu Ser Asp Leu His Glu Ala Val Pro Thr Val
        50                  55                  60

Val Gly Ile Pro Asp Gly Thr Ala Val Val Gly Arg Ser Phe Arg Val
65                  70                  75                  80

Thr Ile Pro Thr Asp Leu Ile Ala Ser Ser Gly Asp Ile Ile Lys Val
                85                  90                  95

Ser Ala Ala Gly Lys Glu Ala Leu Pro Ser Trp Leu His Trp Asp Ser
            100                 105                 110

Gln Ser His Thr Leu Glu Gly Leu Pro Leu Asp Thr Asp Lys Gly Val
        115                 120                 125

His Tyr Ile Ser Val Ser Ala Thr Arg Leu Gly Ala Asn Gly Ser His
    130                 135                 140

Ile Pro Gln Thr Ser Ser Val Phe Ser Ile Glu Val Tyr Pro Glu Asp
145                 150                 155                 160

His Ser Asp Leu Gln Ser Val Arg Thr Ala Ser Pro Pro Gly Glu
                165                 170                 175

Val Val Ser Ser Ala Cys Ala Ala Asp Glu Pro Val Thr Val Leu Thr
            180                 185                 190

Val Ile Leu Asp Ala Asp Leu Thr Lys Met Thr Pro Lys Gln Arg Ile
        195                 200                 205

Asp Leu Leu His Arg Met Arg Ser Phe Ser Glu Val Glu Leu His Asn
    210                 215                 220

Met Lys Leu Val Pro Val Val Asn Asn Arg Leu Phe Asp Met Ser Ala
225                 230                 235                 240

Phe Met Ala Gly Pro Gly Asn Pro Lys Lys Val Val Glu Asn Gly Ala
                245                 250                 255

Leu Leu Ser Trp Lys Leu Gly Cys Ser Leu Asn Gln Asn Ser Val Pro
            260                 265                 270

Asp Ile His Gly Val Glu Ala Pro Ala Arg Glu Gly Ala Met Ser Ala
        275                 280                 285
```

```
Gln Leu Gly Tyr Pro Val Val Gly Trp His Ile Ala Asn Lys Lys Pro
    290                 295                 300
Pro Leu Pro Lys Arg Val Arg Arg Gln Ile His Ala Thr Pro Thr Pro
305                 310                 315                 320
Val Thr Ala Ile Gly Pro Pro Thr Thr Ala Ile Gln Glu Pro Pro Ser
                325                 330                 335
Arg Ile Val Pro Thr Pro Thr Ser Pro Ala Ile Ala Pro Pro Thr Glu
                340                 345                 350
Thr Met Ala Pro Pro Val Arg Asp Pro Val Pro Gly Lys Pro Thr Val
            355                 360                 365
Thr Ile Arg Thr Arg Gly Ala Ile Ile Gln Thr Pro Thr Leu Gly Pro
    370                 375                 380
Ile Gln Pro Thr Arg Val Ser Glu Ala Gly Thr Thr Val Pro Gly Gln
385                 390                 395                 400
Ile Arg Pro Thr Met Thr Ile Pro Gly Tyr Val Glu Pro Thr Ala Val
                405                 410                 415
Ala Thr Pro Pro Thr Thr Thr Lys Lys Pro Arg Val Ser Thr Pro
                420                 425                 430
Lys Pro Ala Thr Pro Ser Thr Asp Ser Thr Thr Thr Thr Arg Arg
            435                 440                 445
Pro Thr Lys Lys Pro Arg Thr Pro Arg Pro Val Pro Arg Val Thr Thr
    450                 455                 460
Lys Val Ser Ile Thr Arg Leu Glu Thr Ala Ser Pro Pro Thr Arg Ile
465                 470                 475                 480
Arg Thr Thr Thr Ser Gly Val Pro Arg Gly Gly Glu Pro Asn Gln Arg
                485                 490                 495
Pro Glu Leu Lys Asn His Ile Asp Arg Val Asp Ala Trp Val Gly Thr
            500                 505                 510
Tyr Phe Glu Val Lys Ile Pro Ser Asp Thr Phe Tyr Asp His Glu Asp
        515                 520                 525
Thr Thr Thr Asp Lys Leu Lys Leu Thr Leu Lys Leu Arg Glu Gln Gln
    530                 535                 540
Leu Val Gly Glu Lys Ser Trp Val Gln Phe Asn Ser Asn Ser Gln Leu
545                 550                 555                 560
Met Tyr Gly Leu Pro Asp Ser Ser His Val Gly Lys His Glu Tyr Phe
                565                 570                 575
Met His Ala Thr Asp Lys Gly Gly Leu Ser Ala Val Asp Ala Phe Glu
            580                 585                 590
Ile His Val His Arg Arg Pro Gln Gly Asp Arg Ala Pro Ala Arg Phe
        595                 600                 605
Lys Ala Lys Phe Val Gly Asp Pro Ala Leu Val Leu Asn Asp Ile His
    610                 615                 620
Lys Lys Ile Ala Leu Val Lys Lys Leu Ala Phe Ala Phe Gly Asp Arg
625                 630                 635                 640
Asn Cys Ser Thr Ile Thr Leu Gln Asn Ile Thr Arg Gly Ser Ile Val
                645                 650                 655
Val Glu Trp Thr Asn Asn Thr Leu Pro Leu Glu Pro Cys Pro Lys Glu
            660                 665                 670
Gln Ile Ala Gly Leu Ser Arg Arg Ile Ala Glu Asp Asp Gly Lys Pro
        675                 680                 685
Arg Pro Ala Phe Ser Asn Ala Leu Glu Pro Asp Phe Lys Ala Thr Ser
    690                 695                 700
```

-continued

```
Ile Thr Val Thr Gly Ser Gly Ser Cys Arg His Leu Gln Phe Ile Pro
705             710                 715                 720

Val Val Pro Pro Arg Arg Val Pro Ser Glu Ala Pro Pro Thr Glu Val
            725                 730                 735

Pro Asp Arg Asp Pro Glu Lys Ser Ser Glu Asp Val Tyr Leu His
            740                 745                 750

Thr Val Ile Pro Ala Val Val Ala Ala Ile Leu Leu Ile Ala Gly
            755                 760             765

Ile Ile Ala Met Ile Cys Tyr Arg Lys Lys Arg Lys Gly Lys Leu Thr
        770             775             780

Leu Glu Asp Gln Ala Thr Phe Ile Lys Lys Gly Val Pro Ile Ile Phe
785                 790             795                 800

Ala Asp Glu Leu Asp Asp Ser Lys Pro Pro Pro Ser Ser Ser Met Pro
                805                 810             815

Leu Ile Leu Gln Glu Glu Lys Ala Pro Leu Pro Pro Pro Glu Tyr Pro
            820             825             830

Asn Gln Ser Val Pro Glu Thr Thr Pro Leu Asn Gln Asp Thr Met Gly
        835             840                 845

Glu Tyr Thr Pro Leu Arg Asp Glu Asp Pro Asn Ala Pro Pro Tyr Gln
    850                 855             860

Pro Pro Pro Pro Phe Thr Val Pro Met Glu Gly Lys Gly Ser Arg Pro
865             870             875                 880

Lys Asn Met Thr Pro Tyr Arg Ser Pro Pro Pro Tyr Val Pro Pro
            885                 890             895
```

DRUG SCREENS BASED ON THE NEWLY FOUND ROLE OF DYSTROGLYCAN PROTEOLYSIS AND RESTORATION OF DYSTROGLYCAN FUNCTION THEREOF

CROSS-REFERENCE TO RELATED APPLICATIONS

This application is a divisional of U.S. patent application Ser. No. 09/652,493, filed on Aug. 31, 2000, currently allowed, which claims priority benefit of U.S. provisional application No. 60/151,766, of filed on Aug. 31, 1999, the contents of both which are incorporated herein by reference in their entirety.

STATEMENT OF GOVERNMENTAL SUPPORT

This invention was made during work supported by U.S. Department of Energy under Contract No. DE-AC02-05CH11231 between the U.S. Department of Energy and the University of California for the operation of Lawrence Berkeley National Laboratory (LBNL). The U.S. Government has certain rights in this invention.

REFERENCE TO ATTACHED SEQUENCE LISTING

This application incorporates by reference the attached sequence listing found in paper and electronic form.

BACKGROUND OF THE INVENTION

Cell growth is highly regulated in normal tissues by a variety of mechanisms in order to guide normal tissue development and homeostasis. A cell's response to the "microenvironment" is a major portion of the growth regulatory machinery. The microenvironment consists of soluble factors, adjacent cell surfaces and molecules of the extracellular matrix (ECM). Information within the microenvironment is primarily detected by cell surface receptors that bind specific molecules found in the micro environment and elicit varied cell responses for growth, morphogenesis or differentiation.

The work reported here focuses on cell interactions with the ECM in general and a specialized form of ECM, called the basement membrane (BM). This specialized extracellular matrix serves not only as a barrier between cell layers, but also as an active signaling substrate that regulates epithelial cell growth, differentiation and tissue architecture. Key signaling components of the BM are the laminin glycoproteins. Laminin-1 alone can induce cell shape changes, growth arrest, and functional differentiation when added to cultured mammary epithelial cells (MECs). Signals from laminin are mediated by direct binding to multiple cell-surface receptors whose individual functions are not completely defined. It has been hypothesized that the aberrant behavior of tumor cells arises, in part, from alterations in cell-BM interactions. In support of this model, tumor cells frequently demonstrate altered responsiveness to BM proteins, indicating changes in BM receptor functions. Significantly, the laboratory of Dr. Mina Bissell has demonstrated that functionally normal MECs can be distinguished from tumorigenic MECs by their growth characteristics when cultured within a 3-dimensional gel of BM proteins (3D-BM assay); functionally normal MECs cultured within Matrigel will grow from single cells to form multi-cellular, polarized acinar structures that arrest growth, whereas tumorigenic MECs grow as disorganized cell masses with unregulated cell growth. The 3-D basement membrane assays distinguish between normal and tumorigenic mammary epithelial cell behavior. Normal cells growth arrest as acinar structures, whereas tumor cells do not growth arrest. This tumor cell characteristic is referred to as a "tumorigenic phenotype". This growth difference has been described in U.S. Pat. No. 5,846,536 incorporated by reference herein. Although it is evident that the cellular machinery that senses the BM is altered in tumorigenic epithelial cells, it is less certain where the critical changes occur. Studies of cell-BM interactions have largely focused on the integrins, an extensively characterized family of heterodimeric receptors. However, integrin signaling generally favors tumor cell growth and metastasis, and no integrin has been unambiguously assigned the role of tumor suppressor, leaving the possibility that other important receptors may still need to be investigated. The present invention relates to the characterization of one such receptor, dystroglycan (DG).

Accordingly, it is an object of the present invention to provide an assay of dystroglycan expression. This assay may be used to show that the laminin binding portion of a-dystroglycan is lost in tumor cells.

It is another aspect of the invention to provide an assay of dystroglycan proteolysis and shedding through the detection of cell-surface α-dystroglycan. This assay focuses on the relative ratio of α- to β-dystroglycan at the surface of cells, as compared to cells like the BT474 cells (FIG. 2, Lane 2) which shed little or no α-dystroglycan.

It is another aspect of the invention to provide an assay for the generation of dystroglycan fragments that can be used to assay for inhibitors of the metaloproteinase(s) cleaving and shedding α-dystroglycan.

It is yet another aspect of the invention to provide an assay that utilizes α-dystroglycan protein, or derivative thereof, as a substrate for a cell-free assay measuring the activity of the protease(s) cleaving it. The substrate consists of either the full-length α-dystroglycan molecule, a fragment thereof, or a synthetic peptide capable of being recognized and cleaved by the enzyme cleaving α-dystroglycan.

BRIEF SUMMARY OF THE INVENTION

The present invention relates to methods and compositions for the diagnosis and treatment of cells lacking normal growth arresting characteristics. This characteristic is referred to as "tumorigenicity," which means the properties of a cell normally associated with tumor forming properties, especially, growth arresting properties, normal cell arrest, and appearance in the 3D-BM assay. Normal, non-tumorigenic cells will be polarized and, in the case of mammary epithelial cells, form acini with regulated growth properties. In the case of tumorigenic cells, the cells are disorganized and sometimes invasive, and exhibit abnormal growth.

It has been found that many tumor cells lack normal cell surface α-dystroglycan and thereby lack dystroglycan function. Re-establishment of dystroglycan function has been achieved in one cell line by transfection and over-expression of the dystroglycan gene. By re-establishing dystroglycan function, the once tumorigenic cells reverted to non-tumorigenic cells which polarized and arrested growth in the presence of basement membrane proteins, demonstrating that dystroglycan functions as a tumor suppressor. Loss of a tumor suppressor function, like that of dystroglycan, facilitates the development of tumors, therefore, cells lacking a tumor suppressor are said to have a higher "potential tumorigenicity." In some cases, loss of a single tumor suppressor, like dystroglycan, can indicate a tumorigenic state, and in other cases additional changes to the cell are required before it becomes capable of forming tumors. For the purpose of this application, either case is described as a higher potential tumorigenicity.

Figure 1:
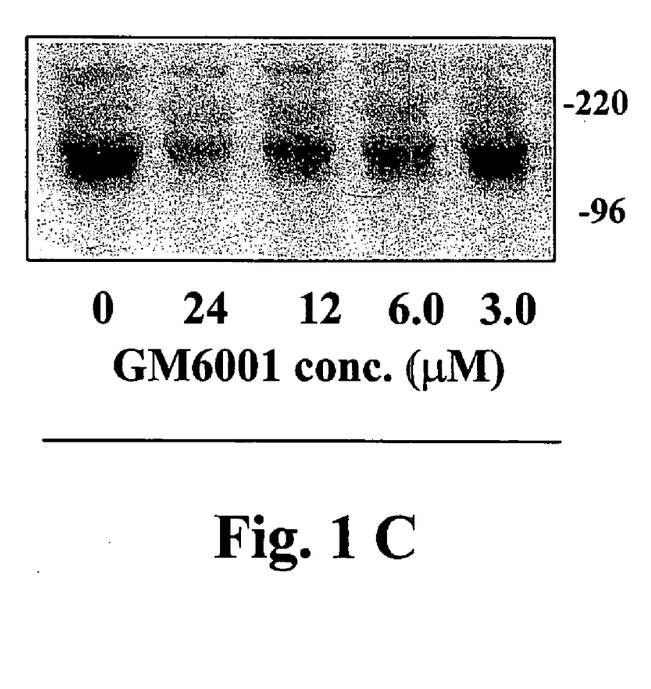
Figure 1A:
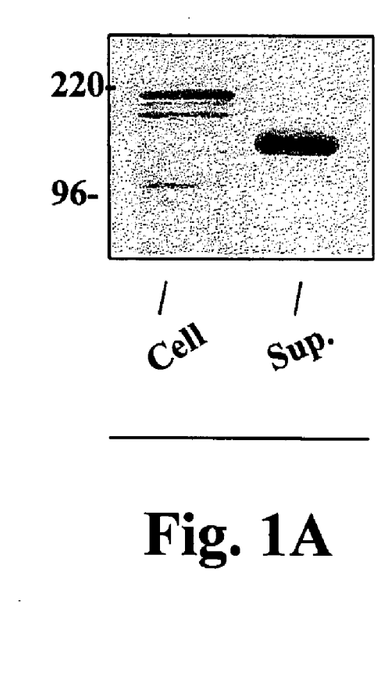

Most importantly, it has been found that dystroglycan can be lost from the cell surface by proteolytic shedding; some tumors cells shed a fragment of α-dystroglycan into the surrounding medium. These forms of α-dystroglycan are distinguishable because normal α-dystroglycan has a molecular weight of ~180 kD, while the shed fragment has a molecular weight (Mr) of 120-130 kD (FIG. 1A). As is known in the field, the term "Mr" refers to relative mobility on electrophoretic gels. This shedding is inhibited by the presence of metaloproteinase inhibitors (FIGS. 1B and 1C).

The present assays may be carried out on tissue samples, the cells themselves, or on the surrounding medium. In vivo, the surrounding medium will comprise the blood and its serum.

Using the above information, one can measure the potential tumorigenicity of cells by assaying for the presence of a fragment of α-dystroglycan in medium, particularly fragments having an Mr of 120-130 kD. Identifying the presence of the α-dystroglycan fragment indicates a higher potential tumorigenicity.

Using the above information, one can also measure the potential tumorigenicity of cells by assaying to determine the ratio of the total amount of α-dystroglycan present in a cell sample relative to the amount of β-dystroglycan present in the sample. A ratio showing a deficiency of α-dystroglycan relative to β-dystroglycan indicates α-dystroglycan shedding.

A correlation between tumorigenicity and the loss of α-dystroglycan through proteolysis has been shown. Treatment of the tumorigenic cells with a metalloprotease inhibitor, at concentrations that inhibit dystroglycan shedding, reverses the tumorigenic phenotype (FIG. 3). Furthermore, treatment of cells with a genetic construct for α-dystroglycan also reverses the tumorigenic phenotype.

The present invention also provides an assay for identifying compounds which can inhibit the cleavage of α-dystroglycan by the endogenous protease that cleaves α-dystroglycan on the surface of cells. The assay comprises the steps of providing test cells, preferably tumor cells, more preferably mammary epithelial tumor cells; adding test inhibitors, along with positive and negative controls; growing the cells; and observing the resultant cell phenotype, i.e., growth arrested (normal phenotype) and tumorigenic phenotype. In cells normally having polarity, the normal phenotype will also involve polarity.

The present invention also provides an assay for identifying compounds that can inhibit the cleavage of α-dystroglycan by the creation of an in vitro assay of dystroglycan proteolysis. The assay comprises the addition of the protease, in a crude protein mixture or in pure form, with a substrate. The substrate consists of either the full-length α-dystroglycan molecule, a fragment thereof, or a synthetic peptide capable of being recognized and cleaved by the enzyme cleaving α-dystroglycan.

One can also use the above information to develop an assay of proteolysed α-dystroglycan fragments in blood serum. This assay would add a labeled antibody specific for an α-dystroglycan or a fragment thereof, and assaying for the amount of bound label present in the serum. As an aspect of this assay, one would look for α-dystroglycan fragments having a Mr of approximately 120 kD.

The present invention also provides a method for suppressing the abnormal growth of tumor cells, or, in effect causing reversion of tumorigenic cells to a normal phenotype. This method involves the addition of a protease inhibitor to the cells, specifically a metalloproteinase inhibitor. The amount of inhibitor to be added can be determined by routine experimentation, in view of the examples provided herein. Metalloproteinase inhibitors may be selected from the group consisting of TAPI, GM6001 or a pharmaceutically acceptable salt thereof, or an ARAM's family protease inhibitor or pharmaceutically acceptable salts thereof. Simply stated, the "effective amount" of metalloproteinase (or protease) inhibitor is reached when the cells to be treated, when grown in culture, specifically the 3D-BM culture system, show normal phenotype and growth arrest, polarity, and secondary organization, such as acini in the case of some mammary epithelial cells.

Finally, one could also use the present invention to restore normal dystroglycan function to a mammalian cell having an abnormal dystroglycan function by contacting a cell with an adenovirus transfection agent containing a normal mammalian dystroglycan gene and a cationic agent which interacts with cell surfaces or nucleic acids so as to result in a cell with said normal functioning dystroglycan gene therein.

BRIEF DESCRIPTION OF THE DRAWINGS

FIG. 1. (FIG. IA) Immuno-detection of α-dystroglycan in SCg6 mammary carcinoma cells revealing a smaller isoform in the culture supernatant (Sup.) than found on the cell surface (Cell). (FIG. 1B) Shedding of α-dystroglycan in the supernatant is blocked by culturing with GM6001, but not in untreated (UT) cells, or in cells treated with the control agent C1004. (FIG. IC) Shedding of α-dystroglycan in the supernatant is differentially blocked by treatment with five different concentrations of GM6001.

FIGS. 3. 3A, 3B, 3C, 3D, 3E, 3F, 3G, and 3H. 3D-BM assays of tumor cell grown in the presence of the metaloproteinase inhibitor with GM6001. (FIGS. 3A, 3B, 3C, 3D) are HMT-3522-T4 (T4) cells; (FIGS. 3E, 3F, 3G, 311) are MDA-MD-231 cells. The cells were either untreated (FIGS. 3A and 3E), treated with 2 μM GM6001 (FIGS. 3B and 3F), treated with 40 μM GM6001 (FIGS. 3C and 3G), or treated with 40 μM C1004 (FIGS. 3D and 3H).

DETAILED DESCRIPTION OF THE PREFERRED EMBODIMENT

Dystroglycan Function

Through assays of normal cell function, we have identified dystroglycan as a laminin receptor signaling cytoskeletal and cell shape changes, and cell growth arrest in normal breast epithelial cells. Dystroglycan is a known transmembrane laminin receptor composed of two non-covalently linked portions: α-dystroglycan and β-dystroglycan; see U.S. Pat. No. 5,449,616 hereby incorporated by reference. These originate from a single protein that is post-ranslationally cleaved. β-dystroglycan is imbedded in the cell membrane. The extracellular chain, α-dystroglycan, binds to laminin. We have shown that inhibition of dystroglycan binding to laminin permits cell spreading and growth in the presence of laminin, conditions where cells would normally round-up and growth arrest. Results suggest a model whereby dystroglycan operates as a co-receptor, which organizes the laminin in the BM and facilitates signaling through other BM receptors. But, dystroglycan is shown to mediate shape changes and growth control without help from β1 and β4 integrins. K. Campbell et al. in Pat. No. 5,449,616 identified dystroglycan using four overlapping clones (designated HD-1 to HD-4) covering the entire mRNA were completely sequenced. The full-length human cDNA consists of 5510 nucleotides (SEQ ID NO: 7, but herein included as SEQ ID NO: 1), of which 2685 nucleotides represent an open reading frame. A polyadenylation sequence and poly(A) tail were also identified. The deduced amino acid sequence (SEQ ID NOS: 7 and 8, herein included as SEQ ID NOS: 1 and 2) predicts a polypeptide of a calculated Mr of 97,552 with a signal sequence of 27 amino acids, a single transmembrane domain close to the C-terminal region, four potential N-glycosylation sites and many potential sites for O-glycosylation.

Alignment of amino acid sequences for human and rabbit dystroglycan demonstrate that both proteins contain 895 amino acids with overall sequence identity of 93%. Ninety percent of the amino acid substitutions are conservative. The transmembrane domain of human dystroglycan is identical to that of rabbit dystroglycan. The intracellular C-terminal region of human and rabbit dystroglycan is highly conserved and is enriched in proline (23%). Both proteins have identical consensus sites for N-glycosylation and have high content of threonine and serine as potential sites for O-glycosylation. High homology between rabbit and human dystroglycan suggests its functional importance, especially in terms of carbohydrate chain attachment sites, since carbohydrates may play an important role in laminin binding.

Because dystroglycan is found to regulate cell growth and cytoskeletal architecture in response to laminin in normal tissues, we have compared these signaling mechanisms in normal and malignant cells in order to ask whether dystroglycan might be altered in tumor cells. Although the β-dystroglycan protein is detected in all tumor cells, the laminin binding portion, α-dystroglycan, was found to be greatly reduced or undetectable in the majority (5 of 8). Loss of α-dystroglycan in these tumor cells was reflected by both the loss of antibody detection and loss of laminin binding ability. Therefore, within this survey α-dystroglycan was functionally absent from 5 of 8 tumor cell lines. As predicted, only those cell lines possessing adequate levels of α-dystroglycan on the cell surface were able to undergo cell rounding in response to laminin. The presence of α-dystroglycan also corresponded with the growth characteristics of tumor cells cultured within a 3D basement membrane. As described earlier, this assay has been employed to distinguish the behavior of tumor cells and normal cell in response to the BM.

Also, as described in Example 5, we have demonstrated that restoration of dystroglycan function to tumorigenic cells can revert the tumorigenic behavior of these cells, restoring normal tissue structure, differentiation potential and growth control. Re establishment of dystroglycan function was achieved in one cell line by transfection and over-expression of the dystroglycan gene. By re-establishing dystroglycan function, the once tumorigenic cells reverted to non-tumorigenic cells which polarized and arrested growth in the presence of basement membrane proteins. Cells over-expressing the dystroglycan gene no longer form tumors after injection in nude mice. This reversion of the tumorigenic phenotype demonstrates that dystroglycan functions as a tumor suppressor.

Receptor Shedding

Because α- and β-dystroglycan are translated originally as a single polypeptide, it was surprising that α-dystroglycan was not detected on the cell surface of many cells when β-dystroglycan was present. We concluded that, by some mechanism, α-dystroglycan was being shed from the cell surface. Shedding could occur by two mechanisms: 1) simple detachment from the cell surface (because α-dystroglycan is non-covalently linked), or 2) shedding induced by proteolytic cleavage of α-dystroglycan or some component attaching α-dystroglycan to the cell surface.

To test these possibilities we looked for the presence of a-dystroglycan in the culture medium of cells which shed the protein and asked if it was proteolytically cleaved. In one mammary carcinoma cell line SCg6, α-dystroglycan was detectable both on the cell surface and in the cell culture medium. Detection was achieved with an anti-α-dystroglycan antibody. One such antibody is described by Durbeej M., Campbell K. P., J. Biol. Chem. 1999; 274(37): 26609-16. Laminin binding may also be used in place of an antibody since α-dystroglycan binds specifically to laminin. However, the α-dystroglycan detected in the medium was approximately ~60 kD smaller than that on the cell surface. This suggested that α-dystroglycan was proteolytically cleaved either before or after shedding. To ask if shedding was induced by the proteolysis, we treated the cells with a general matrix metaloproteinase (MW) inhibitor, GM6001, to see if α-dystroglycan shedding was inhibited. With cells cultured in the presence of 40 μM GM6001, the proteolysed form of dystroglycan was no longer detected in the culture medium (FIG. IB), A control analog, C1004, had no effect at the same concentration.

Therefore, loss of α-dystroglycan from the cell surface is induced by metalloprotease-induced shedding. Titration of GM6001 showed a pKi of approximately 10 μM, and a nearly complete inhibition over 25 μM (FIG. 1C). This represents an unusually high pKi for this inhibitor of metalloproteinases. Most MMPs are inhibited with pKi's of GM6001 below 1.0 μM (Galardy et al., Ann. N. Y. Acad. Sci., 1994. 732: p. 315-23). The results in FIG. 1C indicate that the protease cleaving α-dystroglycan is not among the majority of well-characterized proteases. The best candidates currently are among the ADAMs family of proteases, which are so far the only metalloproteases known to require high concentrations of GM6001 for inhibition. The ADAMs (A Disintegrin And Metalloprotease) are a recently discovered group of multidomain cell surface proteins postulated to play important roles in cell-cell and cell-matrix interactions. For example, ADAM 12 is upregulated in breast and colon cancer, and ADAM 12 supports tumor cell adhesion. Most ADAMs have no assigned substrate and the family is rapidly growing.

The treatment of cells with a matrix metalloprotease inhibitor can inhibit α-dystroglycan shedding and thereby increase α-dystroglycan levels at the cell surface. In turn, as previously demonstrated by gene transfection, restoration of dystroglycan function to the cell surface can restore a normal response to the BM, (i.e. organized cell structure and growth arrest).

Dystroglycan is expressed in all cells of the body, therefore, dystroglycan function and shedding is likely to play an important role in the growth and differentiation of virtually all cells. This suggests that inhibition of dystroglycan shedding may inhibit growth of any cell type, including those contacting the BM such as epithelial and endothelial cells (blood vessels). Because inhibition of endothelial cell growth is an effective therapy against tumor growth itself, an inhibitor of a-dystroglycan shedding will not only revert the tumorigenic characteristics of a tumor cell but also act against tumor growth by inhibiting angiogenesis.

Screens for Therapeutic Compounds

Recognizing that a protease sheds α-dystroglycan from the surface, this protease becomes the target for the action of therapeutic compounds to inhibit the shedding of a-dystroglycan. The use of GM6001 and TAPI to revert the tumorigenic phenotype has demonstrated proof of principle that such compounds can be therapeutic. Therefore, an assay is created for the activity of this protease using as a substrate a peptide containing the cleavage recognition sequences of this metalloprotease.

In one assay, a full-length human α-dystroglycan molecule is added to a physiological solution containing a human protease that cleaves the protein. Cleavage products are detected by separating solution components by size, e.g. through gel electrophoresis, size exclusion chromatography, etc. Test inhibitors are added to the solution and their effect on the creation of fragments by the protease are measured.

Assay for The Detection of Tissue Re-Organization and Cell Growth

We believe α-dystroglycan shedding occurs principally in cells that are reorganizing and growing. Little of such activity occurs in adult tissues, except in cases like the normal processes of mammary gland development, and perhaps angiogenesis. However, such activity would occur on a large scale during hyperplasia or tumor cell growth and the accompanying angiogenesis. α-dystroglycan is shed in two forms, one which binds laminin and a smaller portion with no known binding activity.

Any assay that detects α-dystroglycan proteolysis would be an assay for the detection of tissue re-organization and cell growth. Assays have been created to test for a-dystroglycan proteolysis in cultured cells, tissue sections, and in blood serum. Assays in cell culture include detection of shed a-dystroglycan fragments in the culture medium, and measurement of the ratio of α-dystroglycan to β-dystroglycan on the cell surface. Assays in tissue samples include detection of proteolysed α-dystroglycan fragments by immunoblotting extracted tissues or immunostaining of "nouveau antigens" created by dystroglycan proteolysis. Assays in blood serum include immunologic detection of dystroglycan fragments or nouveau antigens in serum samples.

Normal MEC Function

Using assays of normal MEC function, we divided laminin signaling functions among three different receptor systems, the β1 integrins, α6 β4 integrin, and a yet to be identified "B3 laminin receptor". Most importantly, these results suggested that a non integrin laminin receptor, binding to the E3 domain of laminin, is a critical mediator of cell morphogenesis and growth control in MECs. We now have direct evidence that the "E3 laminin receptor" is dystroglycan. First identified in muscle cells, dystroglycan is now recognized as a laminin receptor expressed in virtually all cell types, including epithelia. We have shown that over-expression of the dystroglycan gene in HMT-3522-T4 cells (T4 cells), which do not respond to laminin in morphogenesis assays, restored correct responsiveness of these cells to laminin. Moreover, these once tumorigenic cells now formed polarized, growth arrested acinar structures in 3D-BM assays, and no longer produced tumors upon injection in nude mice. The reversion of the tumorigenic phenotype of T4 cells by dystroglycan over-expression demonstrates that restoration of dystroglycan function to breast tumor cells can reduce or eliminate their tumorigenic potential, suggesting novel approaches to the treatment of cancer. The role of dystroglycan as a tumor suppressor was, until now, entirely uninvestigated.

Assays in Breast Tumor Cell Lines

Figure 2:
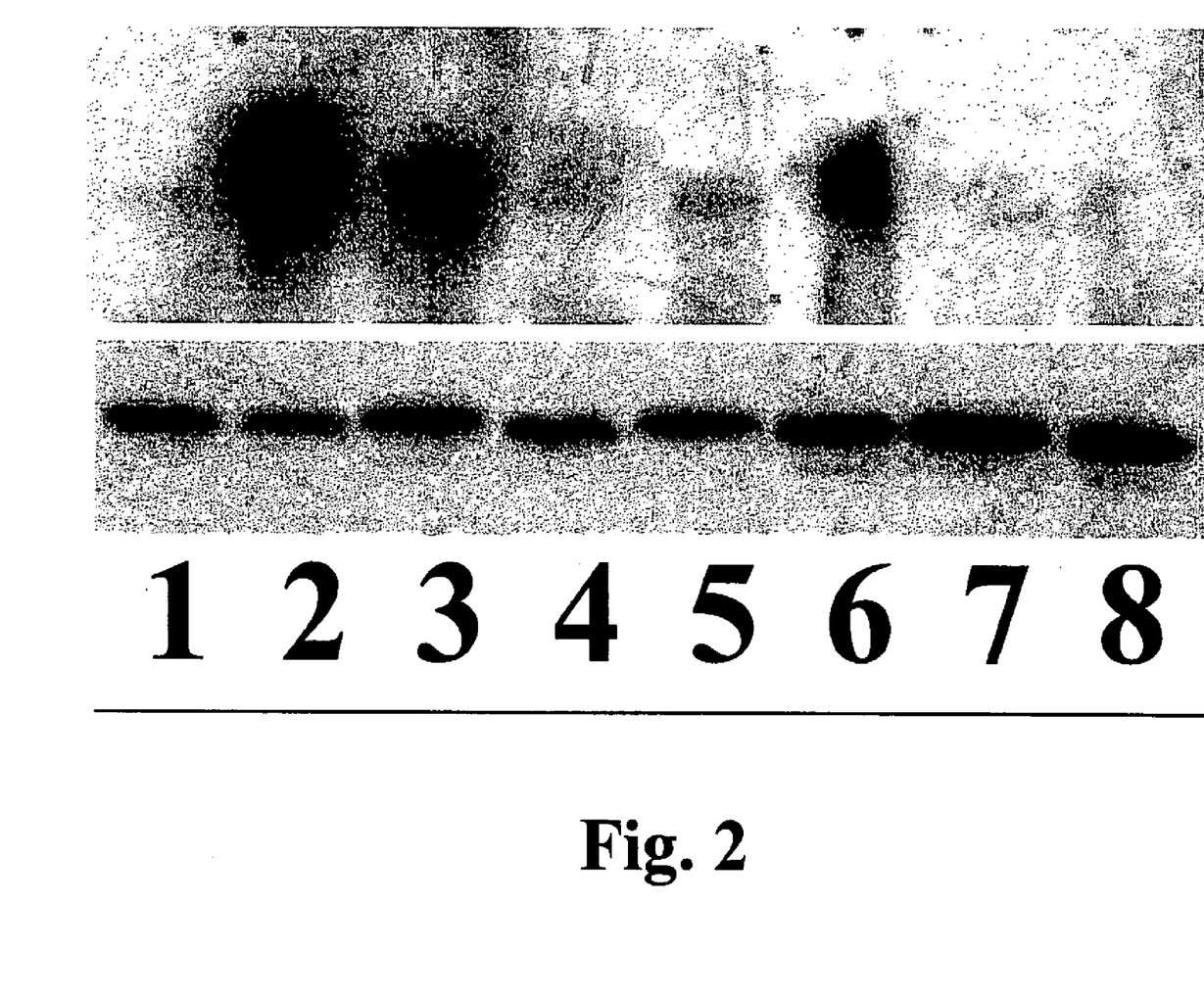
FIG. 2. A photograph of an immunoblot of whole cell extracts from breast tumor cell lines. Immunoblots are shown for both α-dystroglycan (top) and β-dystroglycan (bottom) present on the cell surface. Cell lines used in FIG. 2 are: 1) MCF-7, 2) BT474, 3) Skbr-3, 4) MDA-MD-468, 5) MDA-MD-231, 6) T47D, 7) MDA-MD-435, 8) MDA-MD-453.

Assays of dystroglycan expression in several breast tumor cell lines showed that the laminin binding portion of dystroglycan was lost in the majority of tumor cells. Dystroglycan is composed of two subunits, α and β, which are the product of a single gene that is post-translationally cleaved. Immunoblots showed that the β-dystroglycan subunit was present in all breast tumor cell lines tested, but that the α-dystroglycan subunit, which binds laminin, was greatly diminished or absent in 5 of 8 (FIG. 2). Evidently the α-dystroglycan subunit was shed from the cell surface. Loss of a-dystroglycan in these cell lines correlated with loss of organization in the 3D BM assay and correlated with more aggressive tumor cell behavior in vivo. The ratio of α-dystroglycan to β-dystroglycan is higher in the BT474 cell line, FIG. 2, lane 2, than any other cell line or in normal cells, suggesting that some degree of shedding occurs in all cells, but that shedding is low or absent in BT474s.

In addition, we have demonstrated that shedding of α-dystroglycan can be caused by proteolysis. The α-dystroglycan molecule is detected in the supernatant of some tumor cells, but is smaller than the molecule detected at the cell surface. Shedding of cell surface molecules is most often attributed to cleavage by the ADAM subfamily of metalloproteinases (MPs). Indeed, the action of the hydroxamate MP inhibitor GM6001 implicates an ADAM; shedding of α-dystroglycan is inhibited by GM6001 at a Ki of ~10 μM (FIG. 1C). This Ki is characteristic for some ADAMs but not for other MP's which are generally inhibited by GM6001 concentrations below 30 μM. In addition, the enhanced α-dystroglycan shedding was not detected after conditioned medium from shedding cells was placed on T47D and BT474 cells, again indicating a cell surface-bound MP. Therefore, there is good evidence that α-dystroglycan is shed by the activity of an ADAM or similar MP.

Figure 3A:
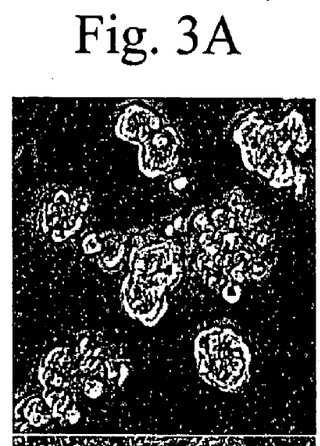
Figure 3B:
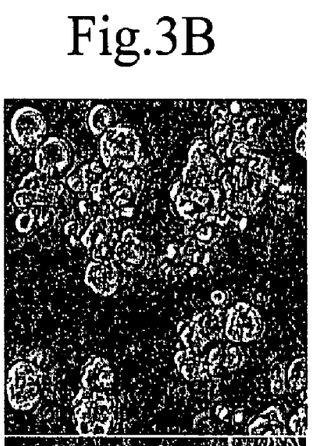
Figure 3C:
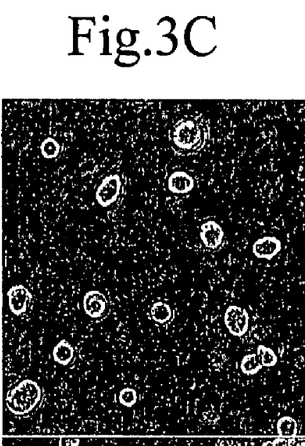
Figure 3D:
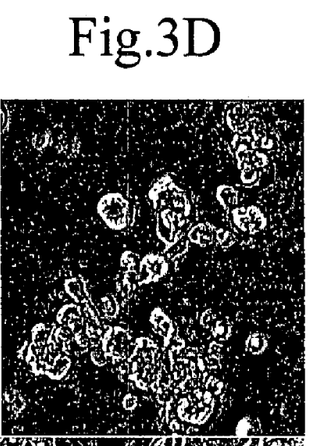
Figure 3E:
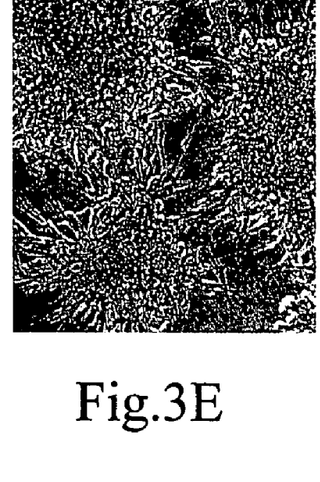
Figure 3F:
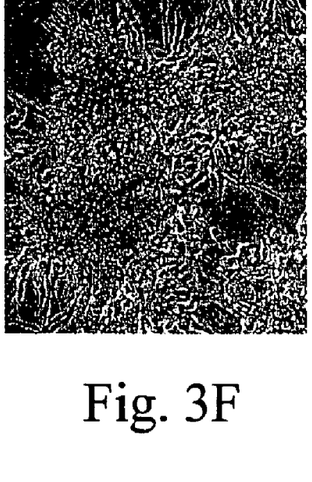
Figure 3G:
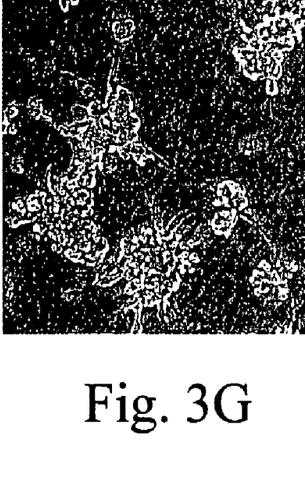

The model drawn above predicts that increasing dystroglycan levels at the cell surface, through inhibition of proteolytic shedding, can revert the tumorigenic phenotype of T4 cells and inhibit the growth of other tumor cells. As shown in FIGS. 3B and 317, treatment with GM6001 at 2 μ.M had no effect on tumor cell growth characteristics in the 3D-BM assay, even though this concentration is sufficient to inhibit most MPs. However, GM6001 concentrations over 20 μM, (sufficient to inhibit dystroglycan shedding) reverted the T4 cells, which formed polarized and growth-arrested acini, and dramatically reduced the growth and invasion of MDA-MD-231 cells (FIGS. 3C and 3G).

Our results, shown in the following Examples, perfectly match those predicted by the model discussed above.

EXAMPLE 1

Assays of Dystroglycan Proteolysis Through Detection of α-dystroglycan Shed from Cell Surface Cleavage of a-dystroglycan was detected using cultured cells that cleave and shed dystroglycan from the cell surface. Dystroglycan cleavage was assayed for by immunoblotting to detect the presence of dystroglycan fragments in the medium of cultured cells. Mammary carcinoma cell lines SCg6 or TCL1 were cultured in 10 milliliters (ml) DMEM/F12 medium supplemented with 2% fetal calf serum, 5 μg/ml insulin (Sigma Chemical Co., St. Louis, Mo.), and 50 μg/ml Gentamycin (UCSF Cell Culture Facility). The cells were allowed to grow to 80% confluence in 10 centimeter (cm) plastic tissue culture dishes. The cells were rinsed two times with phosphate-buffered saline (PBS) and the medium was then changed to 10 mls DMEM/F12 medium supplemented with insulin, and Gentamycin, but without added serum. The cells were incubated in this serum-free medium for 48 hrs, then this conditioned medium was harvested and filtered through 0.4 pm filters to remove cells or cell debris. The harvested medium was concentrated from 10 ml to approximately 1.0 ml using a CENTRIPREP-30 concentrator (Amicon, Beverly, Mass.). The concentrated supernatant was added to 1/10th volume of 10× sample buffer (50% glycerol, 100 mM acetic acid, 10% SDS (w/v), 12.5% (v/v) β-mercaptoethanol, bromophenol blue) and heated at 70 degrees Celsius for 15 minutes prior to loading on SDS-polyacrylamide (SDS-PAGE) gels, and subjected to immunoblot analysis. Assays of dystroglycan cleavage and shedding in the presence of the metaloproteinase inhibitor GM6001 (AMS Scientific, Pleasants Hills, Calif.) were performed in the same manner, with varying concentrations of GM6001, or the control C1004 (AMS Scientific), diluted into the serum-free culture medium at the beginning of the 48 hour incubation. To compare treatments, equivalent volumes of conditioned medium from each treated cell population were loaded onto the gel to determine the relative quantities of dystroglycan shed into the medium.

After separation on an 8% SDS-PAGE gels, the proteins were electrophoretically transferred to Immobilon-P membranes (Millipore Corp., Bedford, Mass.) using methanol transfer buffer (20 mM Tris pH 8.3, 150 mM glycine, 0.5% SDS, 20% methanol). Following the transfer, the membranes were blocked for two hours in low salt TBST buffer (20 mM Tris-HCl, pH 8.0, 100 mM NaCl, 1.0% Tween-20 detergent) plus 5% non-fat dried milk (Lucerne). After blocking, the membranes were incubated for 45 minutes with the IIH6 monoclonal antibody (primary antibody against α-dystroglycan, obtained from Dr. Kevin Campbell, University of Iowa) diluted in low salt TBST plus 5% dried milk. The primary antibody was diluted 1:20 from a concentrated (8×) stock of hybridoma supernatant. After incubation with the primary antibody, the membranes were washed with low-salt TBST and incubated 45 minutes with an horse radish peroxidase (HRP) conjugated secondary antibody (anti-IgM Product #A 8786 from Sigma). The membranes were thoroughly washed for 1 hour after the secondary antibody and the signal detected by chemiluminescence SUPERSIGNAL substrate (Pierce; Rockford, Ill.) and exposure to film. α-dystroglycan that is cleaved and shed from the cell surface appears as a distinct 130 kilodalton (kD) band in the medium (FIG. 1A), whereas β-dystroglycan isolated from the cell surface migrates as a broad 180 kD band (FIG. 1A "Cell").

EXAMPLE 2

Assays of Dystroglycan Proteolysis and Shedding Through Detection of Cell-surface α- and β-dystroglycan Cultured cells were extracted for total protein and immunoblotted for both α- and β-dystroglycan. The ratio of α- to β-dystroglycan in each cell line measures the relative amount of α-dystroglycan retained (or lost) at the cell surface (FIG. 2). Cultured cell were extracted by completely removing the culture medium and adding RIPA extraction buffer [50 mM Tris pH 7.5, 150 mM NaCl, 1.0% NP-40, 0.5% deoxycholate, 0.1% SDS, protease inhibitor cocktail Set 1 from Calbiochem (San Diego, Calif.)] at 1.5 mls for a 10 cm culture dish. The dish containing cells and RIPA was frozen and thawed, then solubilized cells were scraped into an EPPENDORF tube and frozen and thawed a second time. This tube was spun in a microfuge at 13,000 rpm for 5 minutes to pellet any insoluble material, and the supernatant was transfer to a fresh tube. The protein concentration was assayed before adding 10× electrophoresis sample buffer to the extract. Following extraction the proteins were separated on an 8% SDS-PAGE gel, transferred to an Immobilon-P membrane as described in Example 1. The filter was then cut along the level of 60 kD proteins. The top portion of the membrane (proteins 60 kD and larger) was immunoblotted for α-dystroglycan using the IIH6 monoclonal antibody as described in Example 1, above. The bottom portion was immunoblotted for the 43 kD β-dystroglycan molecule using the NCL-b-DG clone 8D5 monoclonal antibody (Novocastra, Newcastle upon Tyne, UK). The immunoblotting procedure for β-dystroglycan was identical to that for α-dystroglycan except the TBST contained higher salt (150 mM). The signals were detected by chemiluminescence (Pierce) and exposure to film or quantitative analysis using the ChemiImager 4000 (Alpha Inotech Corp., San Leandro, Calif.). The ratios of α- to β-dystroglycan were compared within each sample to measure the amount of α-dystroglycan lost from the cell surface. A high ratio of α to β-dystroglycan is evident in the BT474 cell line, which appears to shed little or no α-dystroglycan

EXAMPLE 3

Restoration or Enhancement of Dystroglycan Function in Carcinoma Cells Through Treatment with Metaloproteinase Inhibitors Dystroglycan function reduces the growth potential and induces polarity in normal mammary epithelial cells exposed to basement membrane proteins. As demonstrated in Example 5, restoration of dystroglycan function can induce these events in some tumor cell lines. Because dystroglycan function is lost in part by proteolytic shedding, inhibition of dystroglycan shedding can restore or enhance dystroglycan function. Therefore, restoration of dystroglycan function can be used as an assay for inhibitors of the metaloproteinase(s) cleaving and shedding α-dystroglycan. Carcinoma cell lines, including the HMT-3522-T4 cells and MDA-MD-231 cells, were cultured within the 3-dimensional basement membrane (3-D BM) assay. To accomplish this the cells were trypsinized from routine cell culture, washed once with DMEM/F12 medium, treated with soybean trypsin inhibitor, washed again with DMEM/F12 medium and resuspended in growth medium [DMEM/F12, supplemented with insulin 250 ng/ml (Boehringer Mannheim, Indianapolis, Ind.), 10 µg/ml transferrin (Sigma), 2.6 ng/ml sodium selenite (Collaborative Research), $1.4 \times 10^{-6}$ M hydrocortisone (Collaborative Research), $1 \times 10^{-10}$ M β-estradiol (Sigma), 5 µg/ml prolactin (Sigma)]. The cells were counted and 100,000 cells were resuspended in 0.3-0.5 mls of growth factor-reduced Matrigel (Collaborative Research). This mixture was placed into a 1.5 cm diameter cell culture well, and incubated at 37 degrees Celsius for 30 minutes to induce gelling of the Matrigel. Subsequently, the gelled cell-BM protein mixture was overlayed with growth medium with or without the addition of protease inhibitors or control substances. The cells were cultured at 37 degrees Celsius in a cell culture incubator at 5% carbon dioxide. The growth medium and additives were changed every two days. The additives included GM6001 at concentrations varying from 2 µM to 40 µM, TAPI (Immunex Corp., Seattle, Wash.) at concentrations from 1 to 40 µM, and an inactive control analog of GM6001 named C1004 (used at 40 µM).

GM6001 (N-[2(R)-2(hydroxamidocarbonylmethyl)-4-methylpentanoyl]-L-tryptophane methylamide) is a noncytotoxic synthetic inhibitor that is specific for MMPs. The hydroxamic group of GM6001 binds to the critical active site zinc atom present in MMPs. In addition, the isobutyl group and tryptophan side chain of GM6001 also binds to subsites on MMPs, which normally bind side chains of ECM proteins. (Jones, P L; Crack, J., Journal of Cell Biology, Oct. 6, 1997, 139(1):279-93).

The assay was allowed to proceed from 6 to 10 days. Over this time, the cells grew from single cells within the gel to form multicellular aggregates with variable characteristics, from polarized and growth arrested (normal phenotype), to disorganized and growing (tumorigenic phenotype), to invasive. As observed in FIG. 3, GM6001 concentrations over 20 µM were required to induce polarity in HMT-3522-T4 cells and to reduce the growth potential of MDA-MD-231 cells. Measures of polarity and reduced growth potential can be easily optimized by methods existing in the art.

Beginning at 20 µM GM6001 the tumor cells regained normal cell structures and a growth arrested phenotype. Complete "reversion" of the tumor phenotype was observed at 40 µM GM6001. The reversion by GM6001 was predicted from the observed reversion by dystroglycan over-expression. In addition, the unusually high titration curve of GM6001 required for reversion in the 3D assay was also predicted by the titration of GM6001 in the α-dystroglycan shedding assay (FIG. 1B). Another general MMP inhibitor, TAPI (Immunex Pharmaceuticals), was also observed to revert the T4 tumor cell line at 10 µM concentration. We conclude from these studies that the altered response of tumor cells to the basement membrane results, in part, from the proteolytic shedding of α-dystroglycan from the cell surface.

Removal of the GM6001 for 7 days (following a ten-day incubation with the inhibitor) did not permit a re-initiation of cell growth, indicating that a program of normal cell function was restored, independent of the presence of the inhibitor. This indicates that once dystroglycan function is restored to the cell, signaling from dystroglycan reinforces the message that growth arrest be maintained. It makes sense that proteolysis and shedding of α-dystroglycan is part of a cascade of events used in normal development to facilitate cell growth. Similarly, inhibition of this proteolysis could set the momentum in the opposite direction, leading to sustained reversion of the tumor phenotype.

Figure 3H:
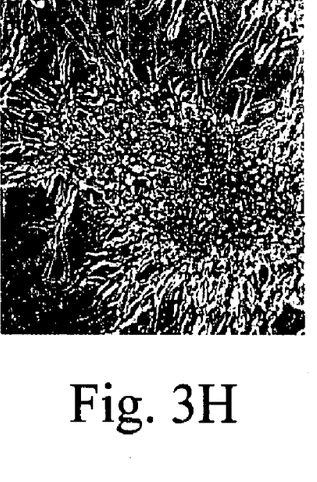

Treatment with 40 µM GM6001 caused growth arrest, polarization and reversion to a non-tumorigenic phenotype (FIG. 3C), and potently inhibited the growth and invasion of MDA-MD-231 cells (FIG. 3G). No effect was observed with 2 µM GM6001 (FIGS. 3B and 3F) or with the control, 40 µM C1004 (FIGS. 3D and 3H).

EXAMPLE 4

In Vitro Assays of α-dystroglycan Proteolysis

The α-dystroglycan protein, or derivative thereof, is used as a substrate for a cell-free assay measuring the activity of the protease(s) cleaving it. The substrate consists of either the full-length α-dystroglycan molecule, a fragment thereof, or a synthetic peptide capable of being recognized and cleaved by the enzyme cleaving α-dystroglycan. Detection of the cleavage event is assayed by any of several methods existing in the art. These methods include, but are not limited to: immunoblotting with a-dystroglycan—specific antibodies to detect proteolytic α-dystroglycan fragments; HPLC or mass spectroscopic analysis of proteolytic fragments, detection of radiolabeled fragments, detection of fluorogenic peptide cleavage. These assays can easily be modified and optimized by a variety of methods existing in the art.

EXAMPLE 4

In Vitro Assays of α-dystroglycan Proteolysis

The α-dystroglycan protein, or derivative thereof, is used as a substrate for a cell-free assay measuring the activity of the protease(s) cleaving it. The substrate consists of either the full-length α-dystroglycan molecule, a fragment thereof, or a synthetic peptide capable of being recognized and cleaved by the enzyme cleaving α-dystroglycan. Detection of the cleavage event is assayed by any of several methods existing in the art. These methods include, but are not limited to: immunoblotting with α-dystroglycan—specific antibodies to detect proteolytic α-dystroglycan fragments; HPLC or mass spectroscopic analysis of proteolytic fragments, detection of radiolabeled fragments, detection of fluorogenic peptide cleavage. These assays can easily be modified and optimized by a variety of methods existing in the art.

The results of this assay will reveal whether, in each sample, some portion of the substrate molecule has been proteolytically cleaved into smaller fragments. Effective inhibitors of the protease will block the creation of the smaller cleavage fragments. This method will be useful for the screening, discovery, selection and optimization of protease inhibitors to be used as therapeutic agents in the treatment of tumor cell growth and other hyperplasias.

EXAMPLE 5

Restoration of Dystroglycan Function Restores Normal Cell Behavior to Tumor Cells The tumorigenic cell line HMT-3522-T4 was found not to round-up in response to laminin when cultured on plastic, indicating that dystroglycan did not function well in these cells. In addition, this cell line is known to not to form organized acinar structures when cultured within a 3-dimensional gel of BM proteins (Matrigel), but instead displays the tumorigenic phenotype of disorganized and uncontrolled cell growth. Therefore, we over-expressed the human dystroglycan gene within these cells to see if, by restoring dystroglycan function, we could restore normal cell behavior to the tumorigenic T4 cells. Identical cells were also infected with an empty virus control (LXSN). We observed that the cells overexpressing the human dystroglycan gene respond to laminin in the medium by aggregating and rounding, whereas the control cells and rabbit dystroglycan expressing cells respond less. Placing these cells in the 3-D assay show that the T4 cells expressing the human dystroglycan gene no longer display the tumorigenic phenotype, but instead arrest growth and form organized acinar structures. Phase photographs of cultures showed the clear difference in colony size and organization; acinar-like structures were formed by cells over-expressing the dystroglycan cDNA, and disorganized structures are formed by the control population. α6 integrin staining showed the polarization of α6 integrins in dystroglycan over-expressing cells and the lack of polarity in the control population. In addition to reverting the tumorigenic phenotype in culture assays, the cells possessing restored dystroglycan function did not produce tumors after subcutaneous injection in to the flanks of nude mice ($5 \times 10^6$ cells/injection), whereas the control cells did. These results reveal the role of dystroglycan as an important suppressor of tumorigenicity in cells. These results also demonstrate that restoration of dystroglycan to tumor cells is a novel therapeutic approach to slow or reverse the progression of cancer.

What is claimed is:

1. A method of restoring dystroglycan function in a tumorigenic mammalian epithelial cell having a loss of dystroglycan function which comprises (a) obtaining an epithelial cell sample suspected of being tumorigenic; (b) identifying cells that have shed a 120-130 kD fragment of α-dystroglycan, whereby the presence of the fragment indicates that said cells are tumorigenic; (c) contacting said cell with a transfection agent containing a mammalian dystroglycan gene SEQ ID NO: 1, whereby the cell comprises a transfected dystroglycan gene therein, and dystroglycan function is restored and the tumorigenicity of said mammalian cell is reduced or reversed.

2. The method of claim 1, wherein said mammalian epithelial cell is a breast epithelial cell.

3. The method of claim 1, wherein the identifying step further comprises:
   a. providing a sample of said cells,
   b. detecting the presence of α-dystroglycan on the surface of said cells,
   c. providing a normal value for α-dystroglycan expression levels on cell surfaces; and
   d. comparing the detection levels of α-dystroglycan to said normal value, whereby a decrease in levels of α-dystroglycan on said cells indicates a cell having a loss of dystroglycan function.

4. The method of claim 3, wherein said detecting comprises:
   a. adding to said sample a monoclonal antibody specific for α-dystroglycan, and
   b. measuring the amount of labeled α-dystroglycan detected.

5. The method of claim 3, wherein the step of providing a normal value comprises measuring the amount of β-dystroglycan on the surface of said cells, wherein a relative decrease in the ratio of α-dystroglycan to β-dystroglycan indicates α-dystroglycan shedding.

* * * * *